(12) United States Patent
Wang et al.

(10) Patent No.: US 10,026,169 B2
(45) Date of Patent: Jul. 17, 2018

(54) RAPID SCREENING DEVICE FOR BRAIN DISEASE

(71) Applicant: Neurobeat Biomedical Technology Corp., Ltd., Taipei (TW)

(72) Inventors: Ching Fu Wang, Taipei (TW); Hai-Jui Chu, Taipei (TW); Chun-Chieh Lee, Taipei (TW); Chien-Hsiu Weng, Taipei (TW); Wei-Cheng Chen, Taipei (TW); Chun-Yi Huang, Taipei (TW); Chin-Hsun Huang, Taipei (TW); Chun-Chen Yang, Taipei (TW); Wai-How Chong, Taipei (TW); Jr Jian Ke, Taipei (TW)

(73) Assignee: NEUROBEAT BIOMEDICAL TECHNOLOGY CORP., LTD., Taipei (TW)

( * ) Notice: Subject to any disclaimer, the term of this patent is extended or adjusted under 35 U.S.C. 154(b) by 0 days.

(21) Appl. No.: 15/174,534

(22) Filed: Jun. 6, 2016

(65) Prior Publication Data
US 2017/0039703 A1 Feb. 9, 2017

Related U.S. Application Data

(60) Provisional application No. 62/171,115, filed on Jun. 4, 2015.

(51) Int. Cl.
*G06K 9/00* (2006.01)
*G06T 7/00* (2017.01)
(Continued)

(52) U.S. Cl.
CPC ............ *G06T 7/0012* (2013.01); *A61B 3/113* (2013.01); *A61B 5/00* (2013.01); *G06T 2207/10004* (2013.01); *G06T 2207/30041* (2013.01)

(58) Field of Classification Search
None
See application file for complete search history.

(56) References Cited

U.S. PATENT DOCUMENTS

| 4,818,091 | A | * | 4/1989 | Sadun | ...................... G02C 7/12 351/224 |
| 4,826,308 | A | * | 5/1989 | Sadun | .................... A61B 3/024 351/232 |

(Continued)

FOREIGN PATENT DOCUMENTS

EP 2853937 A1 * 4/2015 ............. A61B 3/112

OTHER PUBLICATIONS

Frigerio, A., Hadlock, T. A., Murray, E. H., & Heaton, J. T. (2014). Infrared-based blink-detecting glasses for facial pacing: toward a bionic blink. JAMA facial plastic surgery, 16(3), 211-218.*

(Continued)

*Primary Examiner* — Vu Le
*Assistant Examiner* — Samah Beg
(74) *Attorney, Agent, or Firm* — Ming Chow; Sinorica, LLC

(57) ABSTRACT

A rapid screening device has a sensing unit, a processing unit and a carrier, the processing unit is connected to the sensing unit, the sensing unit and the processing unit are disposed on the carrier, the sensing unit captures an image of an eyeball and outputs an image signal of the eyeball, the image of the eyeball is resolved from the image signal of the eyeball, the processing unit retrieves a plurality of images from the sensing unit within a predetermined time interval and executes an algorithm to generate a calculated result by the images of the image signals of the eyeball, and the calculated result is used to diagnose or predict a disease.

6 Claims, 6 Drawing Sheets

(51) Int. Cl.
　　　*A61B 3/113*　　　(2006.01)
　　　*A61B 5/00*　　　(2006.01)

(56) References Cited

U.S. PATENT DOCUMENTS

| | | | | |
|---|---|---|---|---|
| 2007/0121068 A1* | 5/2007 | MacDougall | .......... | A61B 3/113 |
| | | | | 351/221 |
| 2013/0308099 A1* | 11/2013 | Stack | .................... | A61B 3/113 |
| | | | | 351/209 |
| 2014/0171756 A1* | 6/2014 | Waldorf | ................ | A61B 3/032 |
| | | | | 600/301 |
| 2015/0104087 A1* | 4/2015 | Katuwal | .............. | G06T 7/0002 |
| | | | | 382/128 |

OTHER PUBLICATIONS

Kassner, M., Patera, W., & Bulling, A. (Sep. 2014). Pupil: an open source platform for pervasive eye tracking and mobile gaze-based interaction. In Proceedings of the 2014 ACM international joint conference on pervasive and ubiquitous computing: Adjunct publication (pp. 1151-1160). ACM.*

Le, H., Dang, T., & Liu, F. (Dec. 2013). Eye blink detection for smart glasses. In Multimedia (ISM), 2013 IEEE International Symposium on (pp. 305-308). IEEE.*

Abbott, W. W., & Faisal, A. A. (2012). Ultra-low-cost 3D gaze estimation: an intuitive high information throughput compliment to direct brain-machine interfaces. Journal of neural engineering, 9(4), 046016.*

* cited by examiner

RAPID SCREENING DEVICE FOR BRAIN DISEASE

FIELD OF THE INVENTION

The present invention is related to the field of neural diagnosis devices, particularly a rapid screening device for brain disease, which determines symptoms of, for example, cranial nerve by detecting the states of a patient's eyeball(s) and/or the blood velocity.

BACKGROUND OF THE INVENTION

According to clinical statistics, one in every two people may ever have headache in a year, and one in every five people may ever have vertigo in a year. In other words, about 20%~50% of the population suffer from headache and/or vertigo (which are called "symptoms" afterwards.)

Take USA for example, while patients have the symptoms stated above, around 9.6 million patients would resort to the emergency room every year. Take Taiwan for example, while patients have the symptoms, around 0.5 million patients would also resort to the emergency room every year, i.e., averagely more than 1400 patients per day.

Around 90% of the symptoms are benign, meaning they have no effects on the patients, but the other 10% of the symptoms is not appertaining to benignancy such as cerebral palsy, cerebral edema or cerebroma etc. Most of those not appertaining to benignancy stated above require instant treatment in order to avert endangering patients' lives.

However, according to the experiences of emergency physicians and academic statistics, the possibility that the cause of the symptoms is wrongfully diagnosed is about 5% during the diagnosis in an emergency room, and the possibility that the cause of the symptoms diagnosed by an emergency physician is different from that by a medical specialist is even up to 50%. In the 50% possibility, if it happens to be the cause not appertaining to benignancy (of which the possibility is 10%), the instant wrongful diagnosis may result in irreversible consequences.

Conventionally, instruments capable of making precise examination do exist, such as computed tomography (CT) and magnetic resonance imaging (MRI). However, it may be comprehended from certain data that, in the past 10 years, although the number of the patients scanned by the instruments increases, the number of the patients whose cause of the symptoms is certainly determined after scanning decreases. In other words, the results show that it is unnecessary for lots of patients to use the instruments stated above. In USA, adopting CT to scan the patient's brain may cost several hundreds of US dollars while adopting MRI may cost even thousands of US dollars. Therefore, inefficient examinations (i.e., instruments of such precise examination is actually not necessary for all patients) may results in enormous waste in medical cost.

In view of the disadvantages resulting from the inadequacy in instant diagnosis of the symptoms in convention, such as failure of instant diagnosis for serious diseases, missing the golden timing for treatment, causing medical dispute, generating tension in doctor-patient relationship, waste of medical resources and social cost etc., the present invention therefore provides a rapid screening device for brain disease to lower the possibility of wrongful diagnosis and the waste of resources, further raising the survival rate and cure rate of patients.

SUMMARY OF THE INVENTION

A first objective of the present invention is to provide a rapid screening device for brain disease, which is capable of assisting doctors to manipulate neural examination such as headache or vertigo in order to lower the possibility of wrongful diagnosis. The neural examination may be, for example, optic nerve examination (such as examining if there is defect in visual field and if the opening rate of pupils are different, etc.), eyeball examination (such as examining oculomotor, trochlea, strabismus, oscillation of eyeballs (or nystagmus) etc.), trigeminus examination (such as examining the perception of both sides of face), vestibular nerve examination (such as oscillation of eyeballs (or nystagmus) and hearing examination) and facial nerve examination (such as examining the slant of face).

A second objective of the present invention is to provide the rapid screening device for brain disease, which may effectively assist a doctor to diagnose the cause of the headache or vertigo after inquiring a patient's medical history.

A third objective of the present invention is to provide the rapid screening device for brain disease, which can be utilized, for example, at triage in an emergency room or after inquiry by a doctor, in order to enhance the accuracy of diagnosis.

A forth objective of the present invention is to provide the rapid screening device for brain disease, which can be easily operated by a patient first in order to self-conclude if a disease of cranial nerves may possibly happen, is happening or had happened.

A fifth objective of the present invention is to provide the rapid screening device for brain disease so that the diagnosis may be proceeded under the conditions that the patient is conscious, with eye-opening, unconscious, suffering eye disease, with drooping eyelids, with half-closed eyes or with fully-closed eyes.

A sixth objective of the present invention is to provide the rapid screening device for brain disease, which owns advantages of small volume, simple equipment, easy to maintain, convenient to operate in consultation room, low cost, rapid screening, functional check, easy to carry/use and flexible diversity etc.

A seventh objective of the present invention is to provide the rapid screening device for brain disease, which may enhance the accuracy of diagnosis by combining neural-electrical biological examinations and/or determination of the blood velocity.

In order to achieve the abovementioned or other objectives, the present invention provides a rapid screening device for brain disease to diagnose a patient's disease of cranial nerves by the states of the patient's eyeball. The rapid screening device for brain disease comprises a sensing unit, a processing unit and a carrier. The sensing unit is capable of capturing an image of the patient's eyeball. The sensing unit outputs an image signal of the eyeball, wherein the image of at least one eyeball may be resolved from the image signal of eyeball. The processing unit is connected to the sensing unit. The processing unit retrieves a plurality of the images from the sensing unit within a predetermined time interval and the processing unit executes an algorithm to generate a calculated result by the images of the image signals of the eyeball. The carrier is provided with the sensing unit and the processing unit, wherein the calculated result is used to diagnose or predict that the disease happens to the patient.

In another embodiment, the present invention provides a rapid screening device for brain disease which may further combine a biological detection unit, which is capable of detecting the biological states and generating biological signals. The processing unit executes the algorithm to generate the calculated result by the images of the image signals of the eyeball and the biological signal, wherein the calculated result is used to diagnose or predict that the disease happens to the patient.

DETAILED DESCRIPTION OF THE PREFERRED EMBODIMENTS

In order to fully understand the objectives, features and functions of the present invention, the present invention is described in detail as follows by the following specific embodiments along with the accompanying figures.

Figure 1:
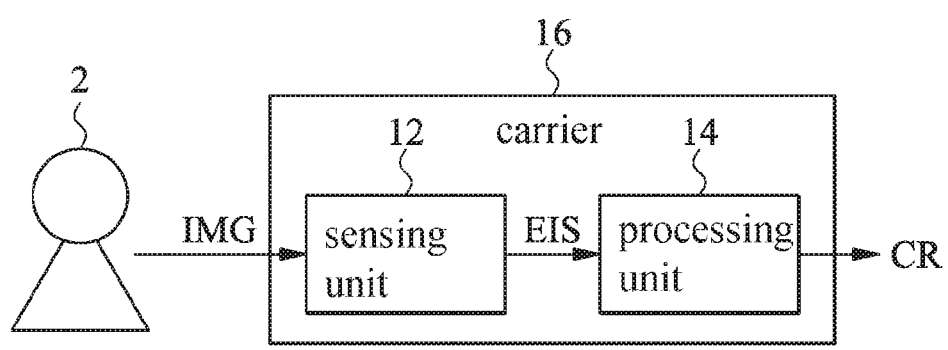
FIG. 1 is a block diagram of a rapid screening device for brain disease in a first embodiment of the present invention.

Refer to FIG. 1, which is a block diagram of a rapid screening device for brain disease in an embodiment of the present invention. In FIG. 1, the rapid screening device for brain disease 10 may be used to diagnose a patient's disease of cranial nerves by the states of the patient's 2 eyeball(s) 2', wherein the states of the eyeball(s) 2' may be oscillation (nystagmus), displacement, eye-opening, eye-closing, structure of eyeball(s) and fundus etc., and the disease of cranial nerves may be apoplexia, cerebral hemorrhage, headache, vertigo and cerebral infarct, etc. Besides, the form factor of the rapid screening device for brain disease 10 may be glasses-clipped-on type, table-machine type, head-mounted type, hand-held type and necklace-hitched type etc. In this embodiment, the rapid screening device for brain disease 10 is described by an example of glasses-clipped-on type.

Figure 2:
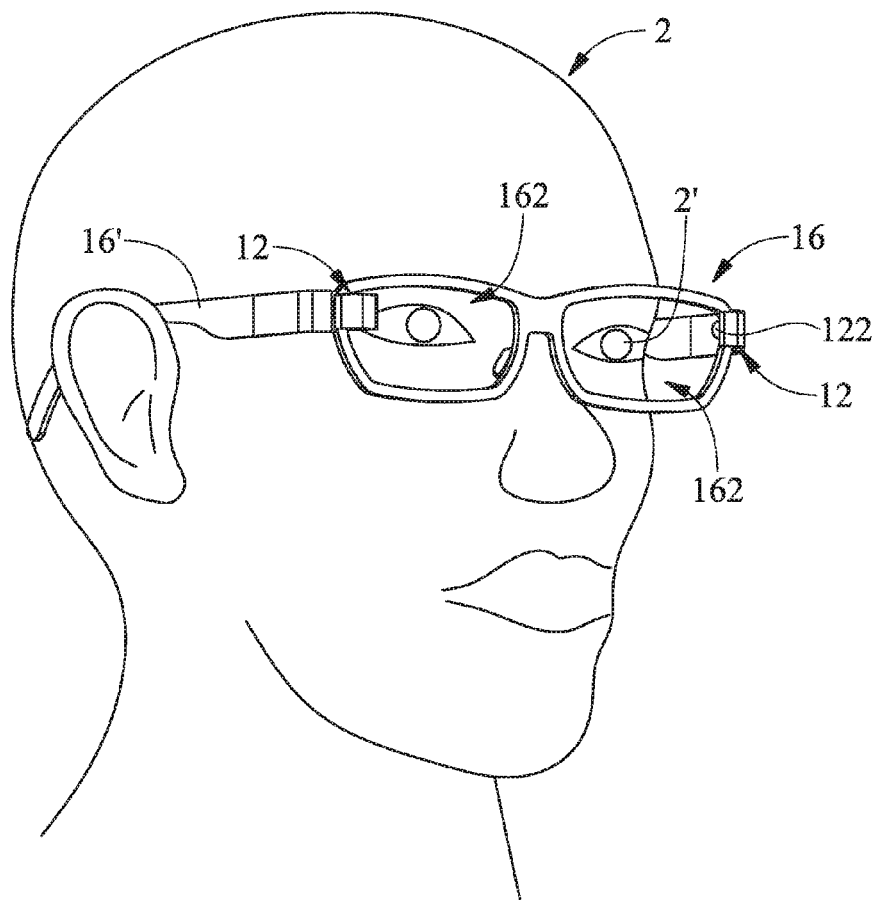
FIG. 2 is a structural diagram to illustrate the rapid screening device for brain disease in FIG. 1.

The rapid screening device for brain disease 10 comprises a sensing unit 12, a processing unit 14 and a carrier 16. Besides, please refer to FIG. 2 as well. FIG. 2 is a structural diagram which illustrates the rapid screening device for brain disease 10 in FIG. 1.

The sensing unit 12 may capture an image IMG of the states of patient's 2 eyeball(s) 2', such as oscillation of eyes, eye-opening, eye-closing and movements of eyeballs, etc. The sensing unit 12 outputs the image signal EIS of the eyeball, wherein the image IMG of at least one eyeball 2' may be resolved from the image signal EIS of the eyeball. The sensing unit 12 may be a single or multiple image capture device(s) 122 and the image capture device(s) 122 is (are) provided at the carrier 16 in order to capture the image IMG of the patient's 2 eyeball 2'. In this embodiment, the sensing unit 12 is described by an example of two image capture devices 122. The image capture device(s) 122 may be CCD, CMOS, as well as CCD or CMOS capable of capturing IR light. It is worthy to note that, the IR-type CCD or CMOS may capture the image IMG of the eyeball 2' illuminated by an IR light source (not shown in the figure) or the image IMG of the eyeball 2' presented under the natural IR light.

The processing unit 14 is connected to the sensing unit 12. The processing unit 14 retrieves a plurality of the images IMG from the sensing unit 12, and the processing unit 14 executes an algorithm to generate a calculated result CR by the images IMG of the image signals EIS of the eyeball, wherein the calculated result CR is related to the symptoms of cranial nerves. In other words, the calculated result CR may be used to diagnose or predict the possibility that the disease may happens to the patient or the patient is suffering from the disease.

For example, the images IMG are the images of eye oscillation. The processing unit 14 may retrieve different images IMG within the predetermined time interval from the sensing unit 12. The processing unit 14 calculates the images IMG by executing the algorithm in methods of analyzing, matching and fitting etc. so that, for example, a displacement of the eyeball 2' in the images IMG within the predetermined time interval may be resolved. The algorithm may determine the frequency of the eye oscillation according to the displacement and the predetermined time interval.

In the present embodiment, the processing unit 14 is provided at the carrier 16. In another embodiment, the processing unit 14 may be dispersively provided at the carrier 16 and remote end (or called cloud).

The carrier 16 is provided with the sensing unit 12 and the processing unit 14. In the present embodiment, the carrier 16 is described by an example of a pair of glasses 16', wherein the patient 2 may be diagnosed with a disease of cranial nerves by wearing the glasses. The carrier 16 forms a plurality of hollow spaces 162. The sensing unit 12 is provided at a side of the plurality of hollow spaces 162 and, by fixing the sensing unit 12, the image IMG of the patient's 2 eyeball 2' can be captured stably. In the present embodiment, the sensing unit 12 is capable of capturing the image IMG directly, and the patient 2 may still view the external environment out of the carrier 16 from the hollow spaces 162 which are not obstructed by the sensing unit 12. In another embodiment, the sensing unit 12 may be provided, for example, at the central part of the hollow spaces 162 as well such that the sensing unit 12 may completely obstruct the vision of the patient 2 from viewing the external environment.

In another embodiment, the rapid screening device for brain disease 10 further comprises a communication unit (not shown in the figure), which may connect at least one of the processing unit 14 and the sensing unit 12. The communication unit complies with the wireless communication standard or wire communication standard. In other words, the communication unit may output at least one of the image(s) IMG and the calculated result CR via wireless or wire communication.

Figure 3:
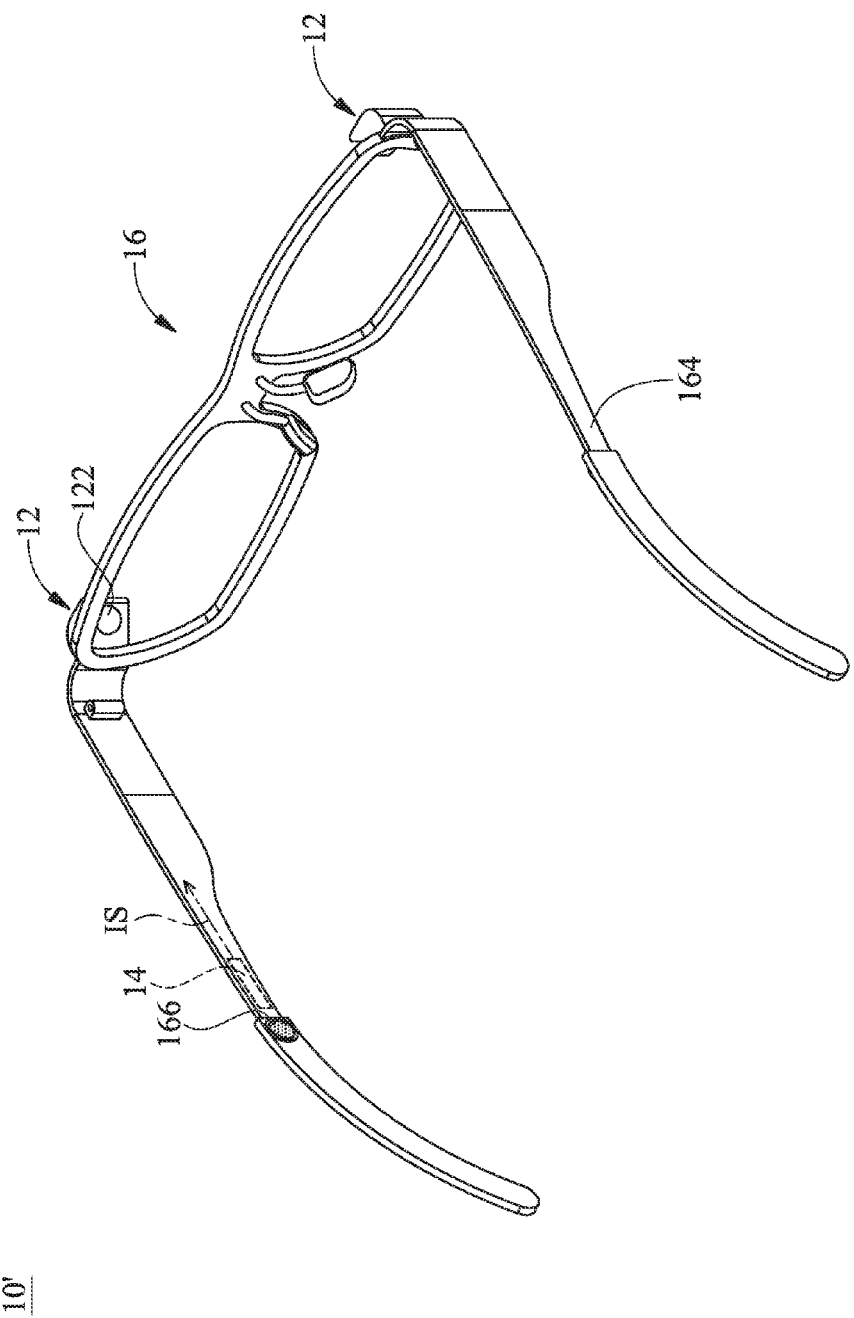
FIG. 3 is a structural diagram of a rapid screening device for brain disease in a second embodiment of the present invention.

Refer to FIG. 3, which is a structural diagram of the rapid screening device for brain disease in a second embodiment of the present invention. In FIG. 3, the rapid screening device for brain disease 10' further comprises an indication unit 18 besides the sensing unit 12, the processing unit 14 and the carrier 16 in the first embodiment.

The indication unit 18 is connected to the processing unit 14. The indication unit 18 receives an indication signal IS from the processing unit 14 in order to instruct the patient 2 to change the states of his/her eyeball 2'. The indication unit 18 may generate at least one of sound, light, temperature, voice message, vibration, electrical stimulation, pressure (such as hydraulic pressure and pneumatic pressure etc.) and force (such as a force to draw the eyelids) in order to instruct the patient 2 to change the states of his/her eyeball 2'. In this embodiment, the indication unit 18 may instruct the patient 2 to control the eyeball 2' to be certain states such as moving left, moving right, moving up, moving down, rolling eyeballs, opening eyes, closing eyes, etc. by the speaker 166 provided at the temple 164 of the glasses 16'.

Meanwhile, the processing unit 14 may simultaneously record at least one of the starting timing, the stopping timing and the indicating direction of the indication signal IS to allow the processing unit 14 being able to determine the relation between the image IMG and the indication signal IS. For example, the image IMG indicates which state that the eyeball 2' is carrying out.

Figure 4:
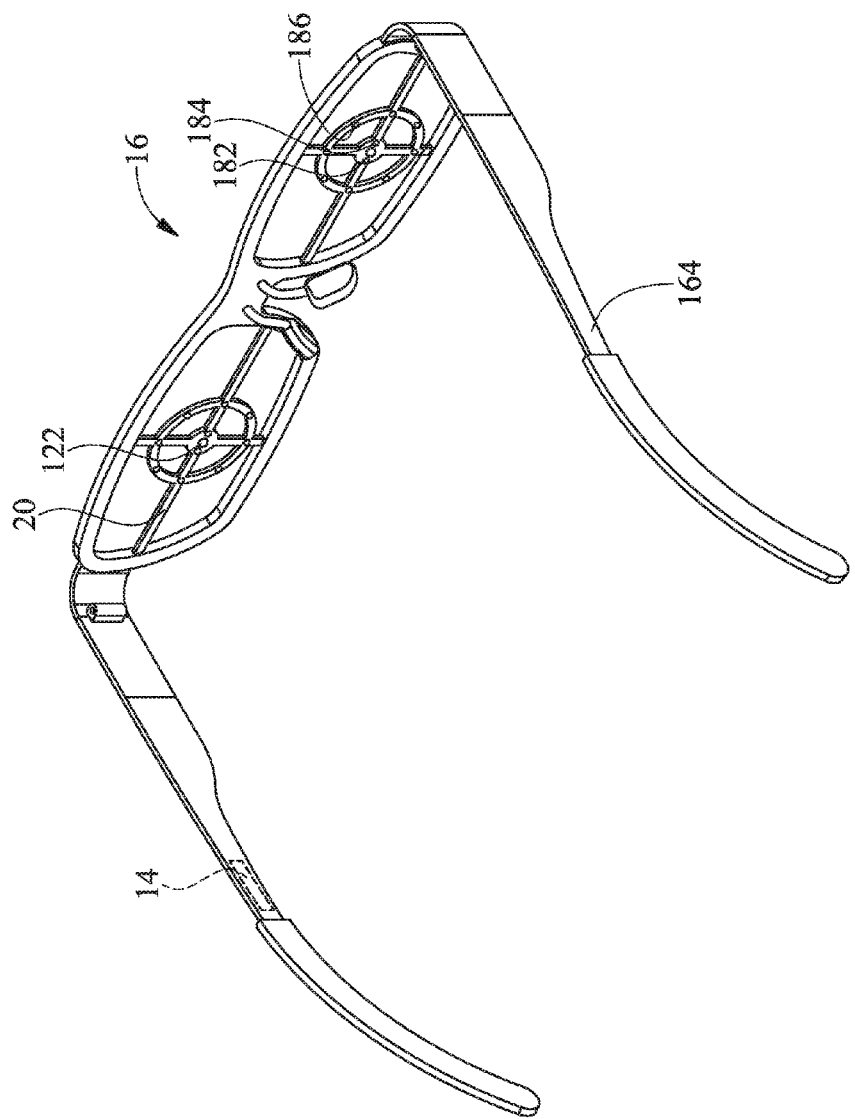
FIG. 4 is a structural diagram of a rapid screening device for brain disease in a third embodiment of the present invention.

Refer to FIG. 4, which is a structural diagram of the rapid screening device for brain disease in a third embodiment of the present invention. In FIG. 4, the rapid screening device for brain disease 10" further comprises a supporting bracket 20 besides the sensing unit 12, the processing unit 14 and the carrier 16 in the first embodiment.

The supporting bracket 20 is provided at the hollow spaces 162. In the present embodiment, the supporting bracket 20 is described by an example of a crossing structure and an annular structure provided in a crossing structure. The sensing unit 12 may be provided on the supporting bracket 20, or the indication unit 18 in the second embodiment may be provided on the supporting bracket 20 as well. The indication unit 18 may be light emitted diodes (LEDs) 182, 184, 186, wherein LED 182 indicates "ready to test", LED 184 indicates the direction that the eyeball 2' shall fixate and LED 186 indicates "test over".

Figure 5:
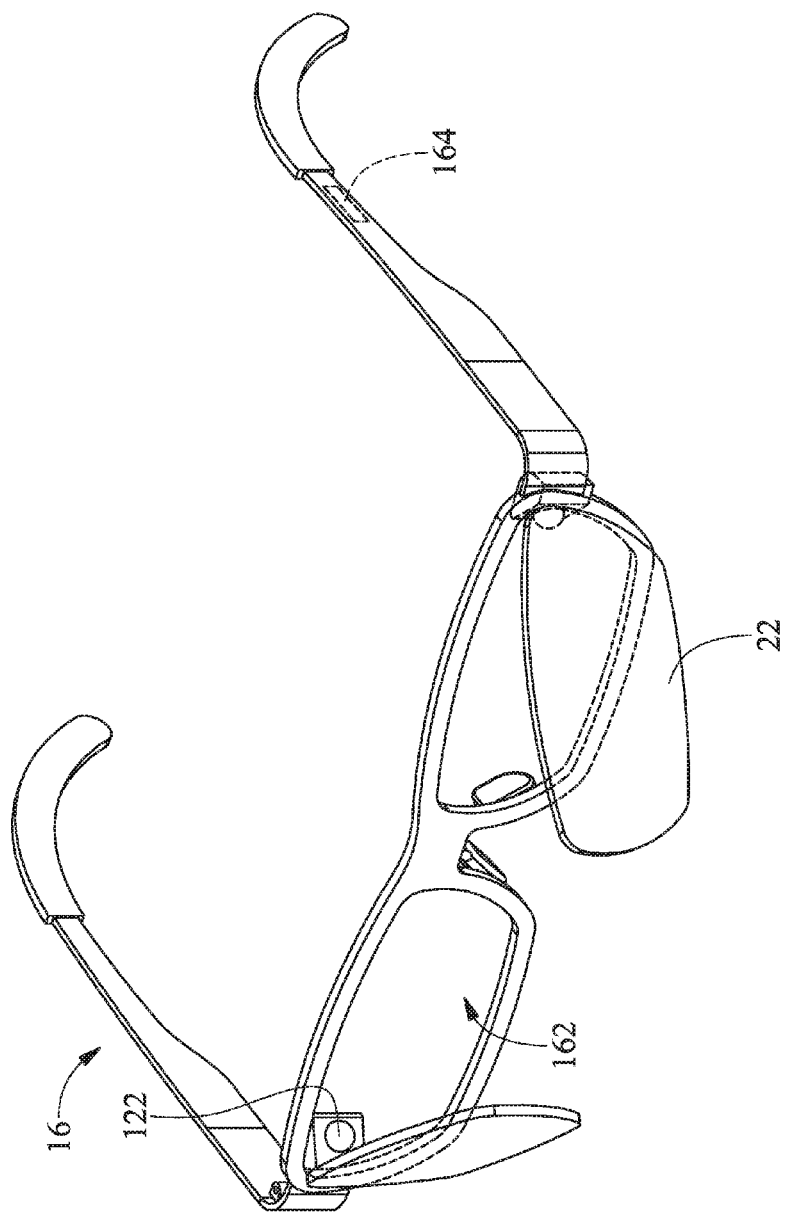
FIG. 5 is a structural diagram of a rapid screening device for brain disease in a forth embodiment of the present invention.

Refer to FIG. 5, which is a structural diagram of the rapid screening device for brain disease in a forth embodiment of the present invention. In FIG. 5, the rapid screening device for brain disease 10''' further comprises a reflection unit 22 besides the sensing unit 12, the processing unit 14 and the carrier 16 in the first embodiment.

The reflection unit 22 is provided at a side of the hollow spaces 162. In the present embodiment, the reflection unit 22 is described by an example of a reflection optical lens with IR reflection coating. The reflection optical lens is capable of reflecting the light with IR spectrum and allowing the light with non-IR spectrum to transmit. The sensing unit 12 captures the image IMG of the patient's 2 eyeball 2' via the reflection unit 22.

Generally, when proceeding diagnosis, the optical intensity of the image IMG is inadequate because the eyeball 2' is obstructed by the carrier 16. The optical intensity of the image IMG may be enhanced by the IR light source (not shown in the figure) so that the image IMG may be directly captured by the sensing unit 12 which is capable of capturing IR spectrum, or the image IMG may be captured by adopting the reflection unit 22 and the sensing unit 12 capable of capturing IR spectrum in the present embodiment.

Figure 6:
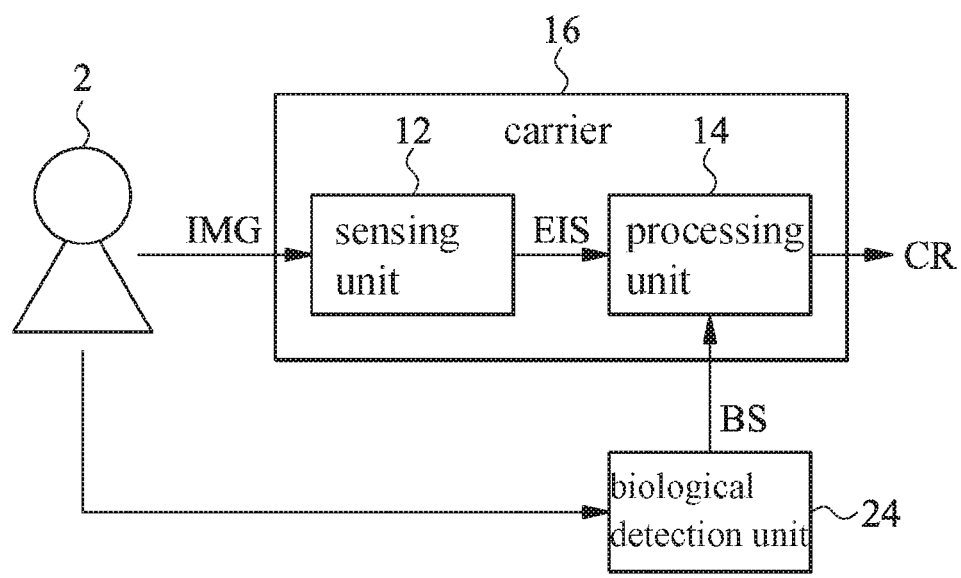
FIG. 6 is a block diagram of a rapid screening device for brain disease in a fifth embodiment of the present invention.

Refer to FIG. 6, which is a structural diagram of the rapid screening device for brain disease in a fifth embodiment of the present invention. In FIG. 6, the rapid screening device for brain disease 10'''' further comprises a biological detection unit 24 besides the sensing unit 12, the processing unit 14 and the carrier 16 in the first embodiment.

The biological detection unit 24 is connected to the processing unit 14 in order to stimulate the patient 2 to generate a biological reaction (such as opening eyes, closing eyes, twitching eyelids, quickened pulses, slowed pulses etc.) and detect the corresponding biological reaction to generate biological signal BS. The processing unit 14 executes the algorithm to generate the calculated result CR by the images IMG of the image signals EIS of the eyeball and the biological signal BS, wherein the calculated result CR is provided to diagnose that the disease happens to the patient 2.

For example, the biological detection unit 24 may carry out biologically neural-electrical stimulation, such as generating local electrical shock at somewhere of the patent's 2 head, to stimulate the patient's 2 biological reaction, and according to the biological reaction generated by the patient 2 while the part is electrically shocked, further provide the biological signals BS corresponding to the biological reaction to the processing unit 14, which allows the processing unit 14 to more accurately determine if the disease happens to the patient 2 based on the biological signal BS and the images IMG.

In another embodiment, the biological detection unit 24 may also carry out the measurement of the blood velocity such as detecting the blood velocity in a vein inside a cranium or a cervical part or the difference of the blood velocity between the vein in the cranium and in the cervical part by a meter, which allows the processing unit 14 to more accurately determine if the disease happens to the patient 2 by the biological signal BS of blood velocity (or the difference of the blood velocity) and the images IMG.

The present invention is disclosed in the abovementioned description by several preferred embodiments, but it is supposed to be comprehended by those who are skilled in the art that the embodiments are used only to illustrate the present invention rather than restrict the scope of the present invention. It should be noted that any equivalent variance or replacement in the embodiments shall be covered by the scope of the present invention. Therefore, what is claimed in the present invention shall be subjected to the claims.

What is claimed is:

1. A rapid screening device for brain disease to determine a patient's disease of cranial nerves by states of the patient's eyeball, the rapid screening device comprising:
   a sensing unit;
   a processing unit;
   an indication unit;
   a carrier;
   the sensing unit comprising an image capture device;
   the image capture device being adapted for capturing a plurality of images of a patient's eyeball within a predetermined time interval by outputting a plurality of image signals of the eyeball and resolving the plurality of image signals of the eyeball;
   the processing unit being electrically connected with the image capture device;
   the processing unit being adapted for generating a calculated result by retrieving the plurality of images from the image capture device and executing an algorithm to the plurality of images of the eyeball;
   the indication unit being electrically connected with the processing unit;
   the indication unit being adapted for receiving an indication signal from the processing unit;
   the calculated result being used to diagnose or predict that a disease happens to the patient;
   the image capture device, the processing unit and the indication unit being disposed on the carrier;
   the carrier comprising a hollow space and a supporting bracket;
   the supporting bracket being accommodated within the hollow space;
   the image capture device being disposed on the supporting bracket;

the indication unit comprising a light emitted diode;
the light emitted diode being disposed on the supporting bracket;
the supporting bracket comprising a crossing structure and an annular structure;
the annular structure being connected with the crossing structure in an intersectional manner;
the annular structure surrounding an intersecting portion of the crossing structure;
the image capture device being disposed on the intersecting portion; and
the light emitted diode being disposed on the annular structure.

2. The rapid screening device of claim 1, wherein the indication unit receives the indication signal from the processing unit in order to instruct the patient to change states of the eyeball.

3. The rapid screening device of claim 1, wherein the calculated result records at least one of a starting time, a stopping time and a direction of indication, which are generated by the indication signal.

4. The rapid screening device of claim 1, wherein the indication unit is used to generate at least one of a sound, a light, a temperature, an electrical stimulation, a pressure, a force, a voice message and a vibration.

5. The rapid screening device of claim 1, further comprising a communication unit, which is connected to at least one of the processing unit and the sensing unit, and the communication unit outputs at least one of the image and the calculated result.

6. The rapid screening device of claim 1, further comprising a biological detection unit which is connected to the processing unit in order to stimulate the patient to generate a biological reaction and detect the corresponding biological reaction to generate a biological signal, wherein the processing unit executes the algorithm to generate the calculated result by the images of the image signals of the eyeball and the biological signal, wherein the calculated result is used to diagnose that the disease happens to the patient.

* * * * *